(12) United States Patent
Wang et al.

(10) Patent No.: US 9,677,130 B2
(45) Date of Patent: Jun. 13, 2017

(54) METHODS TO DETECT AND QUANTIFY RNA

(75) Inventors: Kai Wang, Bellevue, WA (US); Shile Zhang, Gaithersburg, MD (US); David Galas, Seattle, WA (US)

(73) Assignee: Institute For Systems Biology, Seattle, WA (US)

( * ) Notice: Subject to any disclaimer, the term of this patent is extended or adjusted under 35 U.S.C. 154(b) by 17 days.

(21) Appl. No.: 13/397,572

(22) Filed: Feb. 15, 2012

(65) Prior Publication Data

US 2012/0283106 A1 Nov. 8, 2012

Related U.S. Application Data

(60) Provisional application No. 61/443,113, filed on Feb. 15, 2011.

(51) Int. Cl.
*C12Q 1/68* (2006.01)
*C40B 20/00* (2006.01)

(52) U.S. Cl.
CPC ......... *C12Q 1/6851* (2013.01); *C12Q 1/6883* (2013.01); *C12Q 2600/178* (2013.01); *C40B 20/00* (2013.01)

(58) Field of Classification Search
USPC .............................................. 435/6.12, 6.11
See application file for complete search history.

(56) References Cited

U.S. PATENT DOCUMENTS

2009/0220969 A1* 9/2009 Chiang et al. .................... 435/6
2011/0117559 A1* 5/2011 Behlke et al. .................... 435/6

OTHER PUBLICATIONS

International Search Report and Written Opinion for PCT/US12/25299, mailed May 30, 2012, 6 pages.
Lee et al., "MicroRNAs in Cancer," Annu. Rev. Pathol. Mech. Dis. (2009) 4:199-227.
Lu et al., "Construction of small RNA cDNA libraries for deep sequencing," Methods (2007) 43:110-117.
Uziel et al., "The miR-17~92 cluster collaborates with the Sonic Hedgehog pathway in medulloblastoma," PNAS (2009) 106(8):2812-2817.

* cited by examiner

*Primary Examiner* — Kaijiang Zhang
(74) *Attorney, Agent, or Firm* — Morrison & Foerster LLP (57) ABSTRACT

Improved methods to quantitate RNA in biological or other analytical samples employ extended RNAs containing adaptors at the 5' end and polyA sequences coupled to a tag at the 3' end. The invention method is particularly useful in quantitating microRNAs as primers can be used that need not complement the non-conserved 3' ends of these molecules.

5 Claims, 4 Drawing Sheets

```
                            SEQUENCE LISTING

<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: synthetically constructed isomiR
<220> FEATURE:
<221> NAME/KEY: misc_feature
<222> LOCATION: (1)...(19)
<223> OTHER INFORMATION: microRNA species miR-451 isomiR 1

<400> SEQUENCE: 1
aaaccgttac cattactga                                                19

<210> SEQ ID NO 2
<211> LENGTH: 20
<212> TYPE: DNA
<213> ORGANISM: Artificial Sequence
<220> FEATURE:
<223> OTHER INFORMATION: synthetically constructed isomiR
<220> FEATURE:
<221> NAME/KEY: misc_feature
<222> LOCATION: (1)...(20)
<223> OTHER INFORMATION: microRNA species miR-451 isomiR 7

<400> SEQUENCE: 2
aaaccgttac cattactgag                                               20

<210> SEQ ID NO 3
<211> LENGTH: 21
<212> TYPE: DNA
<213> ORGANISM: Artificial Sequence
<220> FEATURE:
<223> OTHER INFORMATION: synthetically constructed isomiR
<220> FEATURE:
<221> NAME/KEY: misc_feature
<222> LOCATION: (1)...(21)
<223> OTHER INFORMATION: microRNA species miR-451 isomiR 6

<400> SEQUENCE: 3
aaaccgttac cattactgag t                                             21

<210> SEQ ID NO 4
<211> LENGTH: 22
<212> TYPE: DNA
<213> ORGANISM: Artificial Sequence
<220> FEATURE:
<223> OTHER INFORMATION: synthetically constructed isomiR
<220> FEATURE:
<221> NAME/KEY: misc_feature
<222> LOCATION: (1)...(22)
<223> OTHER INFORMATION: microRNA species miR-451 miRBase sequence
```

```
<400> SEQUENCE: 4
aaaccgttac cattactgag tt                                              22

<210> SEQ ID NO 5
<211> LENGTH: 23
<212> TYPE: DNA
<213> ORGANISM: Artificial Sequence
<220> FEATURE:
<223> OTHER INFORMATION: synthetically constructed isomiR
<220> FEATURE:
<221> NAME/KEY: misc_feature
<222> LOCATION: (1)...(23)
<223> OTHER INFORMATION: microRNA species miR-451 isomiR 5

<400> SEQUENCE: 5
aaaccgttac cattactgag ttt                                             23

<210> SEQ ID NO 6
<211> LENGTH: 24
<212> TYPE: DNA
<213> ORGANISM: Artificial Sequence
<220> FEATURE:
<223> OTHER INFORMATION: synthetically constructed isomiR
<220> FEATURE:
<221> NAME/KEY: misc_feature
<222> LOCATION: (1)...(24)
<223> OTHER INFORMATION: microRNA species miR-451 isomiR 4

<400> SEQUENCE: 6
aaaccgttac cattactgag ttta                                            24

<210> SEQ ID NO 7
<211> LENGTH: 25
<212> TYPE: DNA
<213> ORGANISM: Artificial Sequence
<220> FEATURE:
<223> OTHER INFORMATION: synthetically constructed isomiR
<220> FEATURE:
<221> NAME/KEY: misc_feature
<222> LOCATION: (1)...(25)
<223> OTHER INFORMATION: microRNA species miR-451 isomiR 3

<400> SEQUENCE: 7
aaaccgttac cattactgag tttag                                           25

<210> SEQ ID NO 8
<211> LENGTH: 12
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(12)
<223> OTHER INFORMATION: polyA tail

<400> SEQUENCE: 8
aaaaaaaaaa aa                                                         12
```

METHODS TO DETECT AND QUANTIFY RNA

CROSS-REFERENCE TO RELATED APPLICATION

This application claims priority from U.S. provisional application 61/443,113 filed 15 Feb. 2011. The disclosure of which is herein incorporated by reference in its entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a), is incorporated herein by reference in its entirety for all purposes. The sequence listing is identified on the electronically filed text file as follows:

| File Name | Date of Creation | Size (bytes) |
| --- | --- | --- |
| 655652001300Seqlist.txt | Apr. 3, 2012 | 2,577 bytes |

TECHNICAL FIELD

The invention relates to determination of analytes that are correlated with biological function. More particularly, it concerns an improved method to measure RNA molecule including messenger RNA (mRNA), microRNA (miRNA), and other noncoding RNAs in biological or other samples.

BACKGROUND ART

In recent years, the function of RNA has been greatly expanded from the traditional roles in the protein translation machinery such as messenger RNA and ribosomal RNA to complex regulatory roles such as miRNAs to regulate the expression, splicing and stability of mRNA. Able to accurately profile RNA molecules in a biological sample is necessary to understand the biological system at molecular level and one of the key information to drive the modern systems biology. Two main approaches, hybridization and polymerase chain reaction (PCR) based methods, have been widely used to measure RNA levels; however, these methods are based on prior knowledge on the sequence. Since sequence information is required to generate specific primers (for PCR) and probes (for hybridization) for RNA of interest. These methods have difficulties to accurately measure gene family members with similar sequences. This problem is especially true for a number of noncoding RNA molecules especially miRNA since the sequence length is short, 17 to 25 nucleotide long, and highly similar to each other. Recent development of short high density parallel sequencing technology, Next Generation Sequencing Technology (NextGen), provides a more comprehensive and accurate view of RNA in biological samples. This approach has been used in miRNA profiling as well as to discover new miRNA species; however, the process of preparing sequencing library is tedious and cumbersome which creates problems on the accuracy of measurement. Since miRNA plays important roles in various biological processes, it is necessary to quickly and accurately to measure the level of specific miRNA species.

The nature of miRNA, as compared to short interfering RNA (siRNA), as currently understood is described, for example, in Lee, Y. S., et al., Annu. Rev. Pathol. (2009) 4:199-227. RNA interference with gene expression can be mediated by either siRNA or miRNA. The functional siRNA consists of small double-stranded RNA, while miRNA is single-stranded. The precursor of miRNA is double-stranded and each strand of the miRNA precursor can form functional mature single-stranded miRNA. The mature miRNA is approximately 17-25 nucleotides in length, while siRNA is double-stranded RNA each strand containing about 20-30 nucleotides.

The siRNA that effects gene (or messenger RNA (mRNA)) silencing is formed from cleaving longer double-stranded RNA by Dicer. The sequences of the siRNA correspond to the coding regions of the gene of interest. The short double-stranded synthetic siRNA can also be fed directly to cells to silence the expression of specific gene sequence. The siRNA enters the RNA induced silencing complex (RISC) and represses expression mostly, it is believed, by degradation of targeted gene.

MicroRNA is synthesized in the nucleus initially as pri-miRNA which is then processed to pre-miRNA, a double-stranded RNA molecule with hairpin structure, by the enzyme Drosha. The pre-miRNAs are exported into the cytoplasm by protein called exportin and are then cleaved by Dicer to form a short double-stranded RNA. Usually one of the strands is then incorporated into the RISC to repress translation or the stability of targeted messenger RNAs. The nucleotide sequences in miRNA are generally derived from non-coding portions of the genome including sequences between protein coding genes and introns of protein coding genes. The miRNA usually interacts with the untranslated regions such as the 3' or 5' untranslated region of protein encoding mRNA. The actual mechanisms whereby miRNA results in reduction of either protein translation or stability of protein-encoding genes are not completely understood, and appear to differ in various miRNA-mRNA interactions.

A multiplicity of miRNAs is known from many organisms. As of the publication of the above-referenced Lee article, there were more than 5,000 miRNAs from over 50 organisms registered in the database (miRBase release 10.0 August 2007).

The specificity of miRNA is believed to be determined mainly by the first eight nucleotides, labeled the "seed sequence." Apparently, however, the current algorithms to predict their interacting mRNA targets for the various miRNAs are imperfect. The experimental verification of miRNA interacting targets usually involves fusion of a luciferase reporter to the 3'UTR of the putative target mRNA and showing that light emission is diminished by overexpression of the miRNA.

The terminology applied to microRNA is becoming standardized. It is named as miR plus numbers and miRNAs of similar sequence usually are distinguished by an additional letter following the number—miR-130a and miR-130b will be similar. An additional number is added, e.g., miR-130a-1 if species of the same nature miRNA arise from different genomic loci and have different precursor sequences. The end regions, especially the 3' end, of miRNAs usual show some length variations. These miRNA sequences, which are derived from the same precursor, are termed isomiR's. This 3' end sequence heterogeneity may affect the accuracy of miRNA level measurement.

Measurement of particular miRNAs is important in a number of contexts because of the variety of important roles miRNAs play in biological activities, including differentiation, proliferation and cell death. Metabolic activities, such as circadian rhythm and neurotransmitter synthesis also appear to be regulated by miRNAs. Thus the ability of accurately assessing the miRNA spectrum in a biological system is important. However, the nature of miRNA sequence including the very short length of the miRNA sequences as well as highly similar miRNA sequences in the cells makes the measurement problematic, since it makes the designing of primers or probes for specific miRNA difficult. The existence of large number of isomiR's worsens the problem of assessing the level of miRNA accurately.

Several commercially available miRNA measurement platforms are available including microarray based and quantitative polymerase chain reaction (qPCR) based methods. The general detection principles for these methods are well known in the field.

The microarray-based method usually involves the spotting or synthesizing miRNA specific probe sequences on a solid surface, such as glass. The array is then hybridized with florescent or color matrix dye-labeled microRNAs from biological samples. The miRNA levels are then determined by the intensity of fluorescent or colored dyes.

Figure 1:
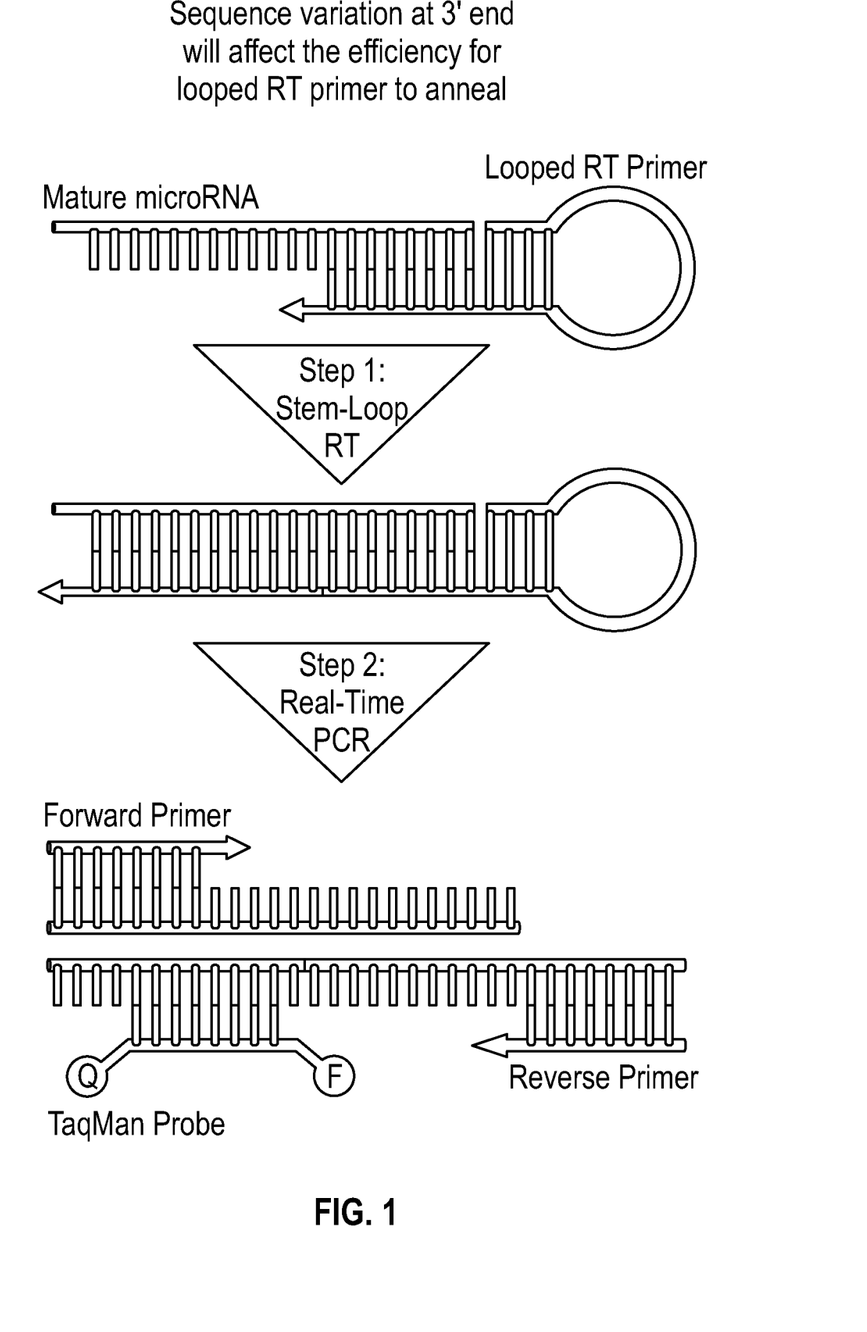
FIG. 1 shows a diagram of miRNA detection marketed by Life Technologies.

The qPCR based systems generally involve modification of the miRNA templates so that they are long enough to support two independent primers that are required for PCR. In one method, marketed as TaqMan® by Life Technologies, a hairpin nucleic acid molecule with one prong shortened and the other extended to be complementary to the 3' portion of the targeted miRNA is first annealed to the miRNA in the sample. The longer arm of the hairpin is then further extended by using the miRNA as a template to generate miRNA cDNA. (see FIG. 1). The loop is then opened to serve as an adaptor for extension of the original microRNA thus resulting in a longer RNA molecule for amplification. The amplified molecule is detected with a probe containing a fluorescence quenching system.

Figure 2:
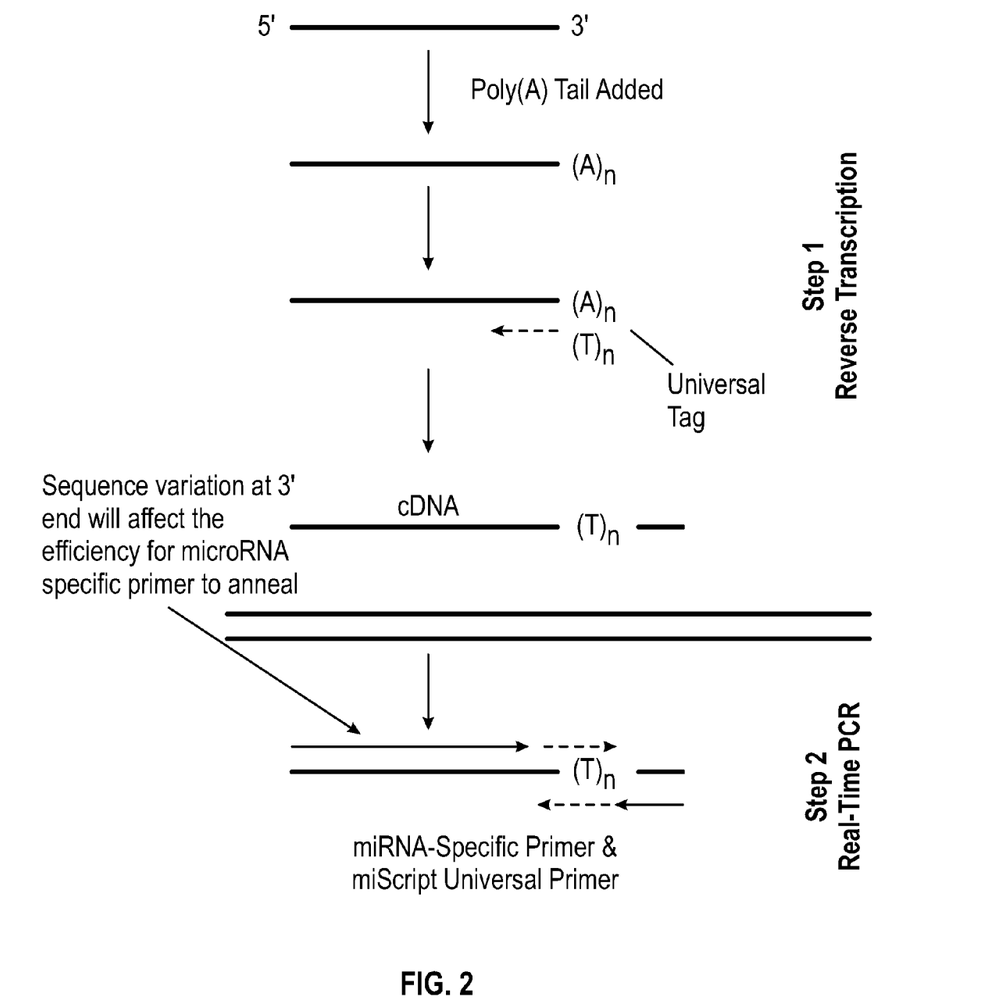
FIG. 2 shows a diagram of miRNA detection marketed by Qiagen.

In another system, marketed by Qiagen, a polyA tail is added to the miRNA. The miRNA is then transcribed into cDNA by annealing a polyT with a tag sequence to the polyA. The resulting cDNA can then be used in detecting specific miRNA by PCR using an miRNA specific primer and a polyA primer with a tag sequence at 3'end. (See FIG. 2.) The miRNA specific primer usually covers the entire length of the miRNA because of the short sequence of the miRNA.

An additional system, Exiqon, uses a similar approach to that of Qiagen but with different tag sequence. It incorporates modified nucleotides into the primer to provide "locked" nucleic acid, to increase primer specificity.

All of these systems suffer disadvantages, especially because they are dependent on integrity of miRNA sequence at the 3' end, which is known to be variable within miRNA-isomiR's. The method of the invention offers an improvement that obviates the effect of 3' end variations by adding adaptors at the 5' end, which is more conserved.

DISCLOSURE OF THE INVENTION

The invention provides more reliable and flexible assessment of the spectrum of miRNA as well as other RNA molecules in a sample by providing specific tag sequences at both the 5' and 3' ends. The method begins by breaking down any large RNA molecules into smaller pieces using chemical modification or sonication. A 5' adaptor sequence is added to the RNA molecules either by ligating a RNA adaptor or by adding it during cDNA synthesis as described below. A polyA tail is incorporated to all RNA molecules in the sample with polyA polymerase. The polyA sequence is used as a template for cDNA synthesis using an anchored complementary polyT oligonucleotide coupled to a specific tag sequence at the 3' end. After converting the RNA into cDNA, all cDNA molecules in the sample should have a 5' adaptor as well as the tag sequence at the 3' end. (In the complement, the polarity is reversed and the complement to the adaptor is at the 3' end, etc.) This pool of cDNA can then be used to assess the global spectrum of RNA molecules including mRNAs, miRNAs and other noncoding RNAs by various known methods.

There are several options to assess spectrum of RNA including mRNA, miRNA and other RNA of interest by qPCR. For mRNA, the level of expression of specific genes can be assessed by using either 3' tag or 5' adaptor primer with a gene-specific primer. To determine the level of miRNA, one version is to use primers specific to the 5' adaptor sequence as well as primer specific to the miRNA of interest. Another version is to use the 3' tag and primer specific to the miRNA of interest. Since the adaptor sequence is added on the 5' end, part of the 5' adaptor is used as the primer sequence so that the end of the miRNA primer specific for the 5' portion of miRNA stops short of the 3' end of the miRNA, which is known to have significant sequence variations within isomiR's. Another version is to assess the level of specific miRNA precursor by incorporating part of the precursor sequence at the 3' end of PCR primer during the design of miRNA specific primer.

The spectrum of RNA can also be determined with next generation sequencing technology. In this approach the 5' adaptor and 3' tag sequences have to be identical to the adaptor sequences that are used in next generation sequencing library construction such as Illumina and SOLiD so that the cDNA pool can be immobilized on a chip and sequenced. In addition, the size of the cDNA pool also needs to be selected to avoid sequences that just have the adaptors. This sequencing library construction process is simpler, faster and has less manipulation steps than existing methods.

MODES OF CARRYING OUT THE INVENTION

Figure 3:
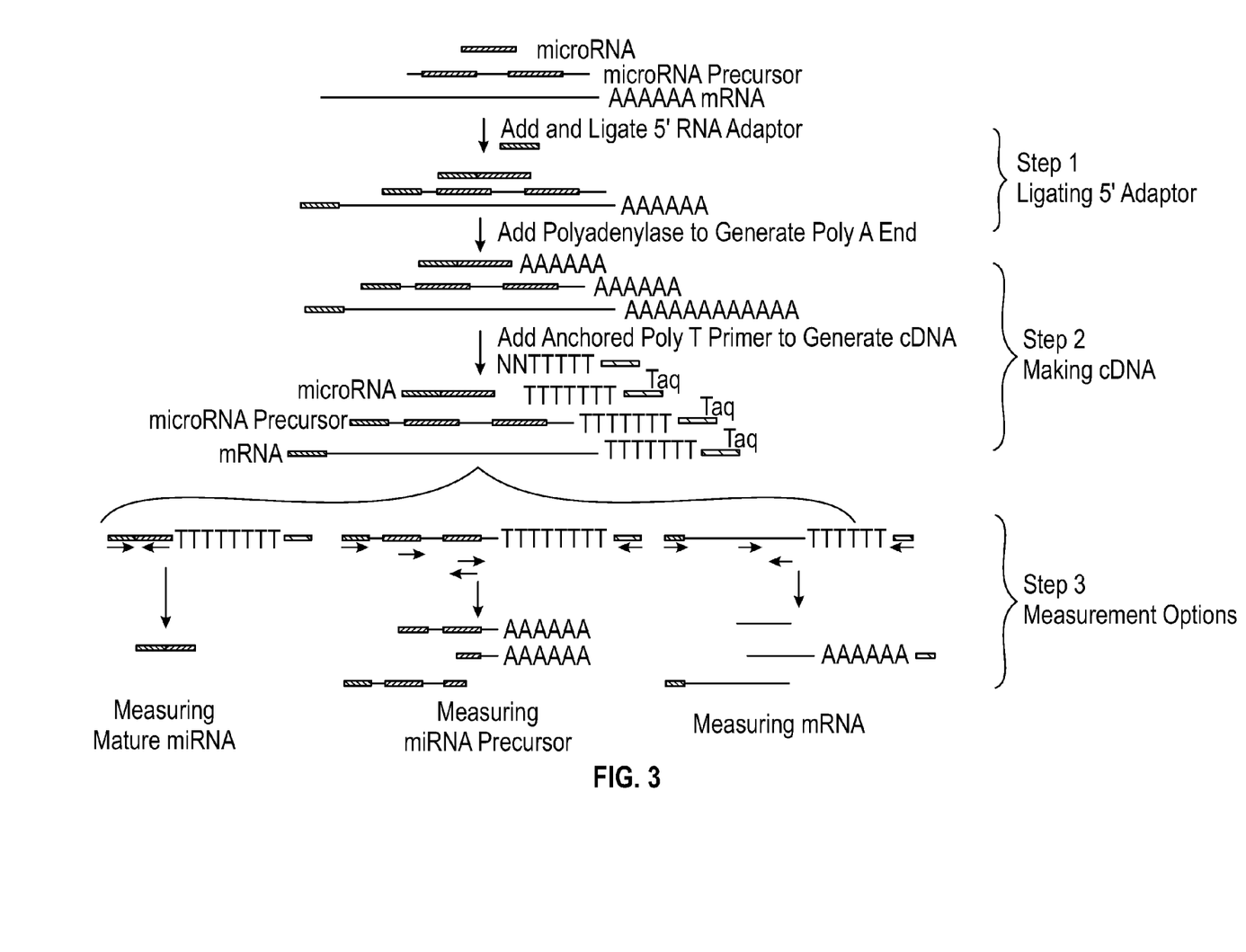
FIG. 3 shows a diagram of miRNA detection method described in the invention method (SEQ ID NO:8).

A diagram of the method of the invention for miRNA detection is shown in FIG. 3. The focus of the method is to measure microRNA, but because the first two steps of the method generate cDNA from all of the RNA molecules, including RNA molecules that usually do not contain poly A tail at the 3' end, any selected RNA can be measured using this method by appropriate choice of primers in the third step. Thus, in addition to miRNA, mRNAs, ribosomal RNAs, tRNAs and any other noncoding RNA present may be assessed.

In step 1 an RNA adaptor typically in the range of 5-40 nucleotides is ligated to the 5' end of all RNA molecules in the samples. This RNA ligation step is known in the art and is used in many different standard protocols. This increases the length of RNA and provides more room for primer and probe design so as accurately and specifically to assess the level of a target RNA molecule. This is extremely important for short and highly similar RNA molecules such as microRNA. The additional nucleotide sequence (the adaptor) added at 5' end of the RNA molecule allows primer or probe sequence to use this adaptor sequence as part of the primer or probe and utilize any specific sequence variations at the 5' end of the RNA molecule to assess the level of specific RNA species.

In step 2 the ligated RNA molecules are converted into cDNA. As in the Qiagen protocol, polyadenylase is added to the sample to incorporate polyA tails at the 3' end of the RNA molecules. A two-base anchored polyT primer with specific tag sequence at the end (anchored nucleotide sequence represented as NN in FIG. 3) is annealed to the end of RNA sequences to serve as primer for reverse transcriptase to generate cDNA. The resulting cDNA should have sequence complementary to the 5' adaptor, the RNA sequence, and to a fixed length of polyA, followed by the known tag sequence. These steps are also well known.

In step 3, the desired RNA to be assessed is preferentially amplified by selecting appropriate primers. Thus, if microRNA is to be detected, primers containing approximately 15-25, or an intermediate number such as 20, 21 or 22 nucleotides are selected as forward and reverse primers for amplification. (All intermediate numbers are included.) Several different options on primer combinations can be used to measure the level of specific miRNA. For example, one primer will contain a sequence of polyA followed by sequence found at the 3' end of the microRNA and the other primer will contain sequence of the adaptor coupled with sequence found at the 5' portion of the microRNA, or one primer contains 3' adaptor sequence and the other primer contains the sequence of the adaptor coupled with sequence found at the 5' portion of the microRNA. By appropriate selection of the unique portions of the sequence, the microRNA is specifically amplified and detected.

As noted above, while focus of the invention is resolving problems associated with amplification of microRNA, the method of the invention can be used to detect and assess any desired RNA in a sample.

One additional use of this method is to generate sequencing libraries for the Nextgen sequencing platforms. The NextGen sequencing platforms provide a powerful and presumably unbiased view of RNA spectrum in sample; however, significant errors in the results can be introduced in the construction of NextGen sequencing library. The NextGen sequencing library preparation protocols are lengthy and cumbersome due to the processes involving adding the sequencing primer sequences onto the RNA population. We can easily construct a sequencing library with the invention method by adapting the NextGen sequencing primer sequences for the 3' and 5' adaptors.

One usage of the invention method is to incorporate specific nucleotide barcodes into the adaptor sequences. This approach is well-known in the art, called multiplexing, by combining different samples in measurement to reduce errors in cross sample comparison and reduce cost. In this approach, different samples will be prepared using the invention method with adaptors containing distinct barcode sequences so that the data obtained can be easily binned into different samples.

miRNAs play important regulatory roles in many cellular processes, including differentiation, neoplastic transformation, and cell replication or regeneration. Aberrant miRNA expression has been implicated in several diseases. Like mRNAs, some miRNAs are differentially expressed among different tissues or developmental stages. Examples include miR-122, which is preferentially expressed in the liver, miR-133a and miR-133b, which are highly enriched in muscle, and the miR-302 family members which are restricted to stem cells. Unlike some widely expressed miRNAs, these tissue- or developmental stage-restricted miRNAs likely play key roles in regulating specific processes involved in the development or specific function of individual tissues. The liver-specific miRNA, miR-122, for example, has been implicated in lipid and cholesterol metabolism, which are both known to be important functions of liver. Because of their restricted expression profiles, these miRNAs hold promise as diagnostic markers or therapeutic targets for tissue- or biological stage-specific diseases. For example, miR-122 is required in hepatitis C virus (HCV) replication and reagents that can modulate the level of miR-122 have moved into clinical development for HCV treatment. Therefore, able to accurately determine the spectrum of microRNA in biological sample is important as the levels and types of microRNA present are indication of various physiopathological conditions.

The following examples are offered to illustrate but not to limit the invention.

EXAMPLE 1

Comparing with Existing QPCR Protocols in microRNA Detection

Synthetic isomiR RNA templates were prepared as shown in Table 1. As noted, only the 3' regions are different (as are most isomiR's); the first 17 nucleotides are identical in all cases.

Figure 4:
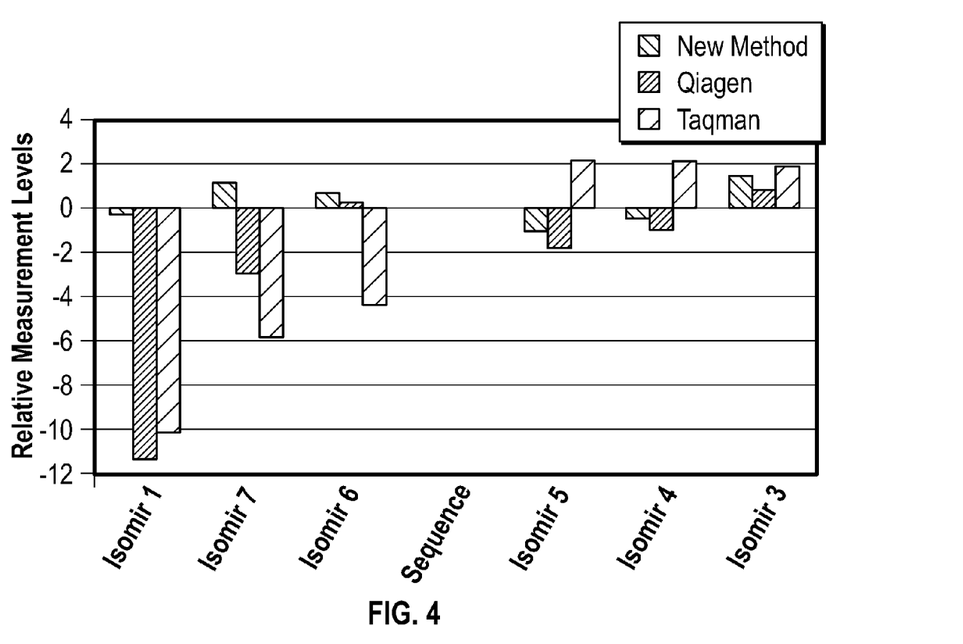
FIG. 4 shows results of comparison of the invention method with prior art QPCR in a standard assay.

Equal amounts of the isomiR's listed in Table 1 were subjected to quantitative PCR (qPCR) measurement using protocol and reagents from Life Technologies (TaqMan®), Qiagen, and the method of the invention, as described above. The same amounts of miR-451, and isomiR's 1 and 3-7 were measured and the relative detection efficiency compared to miR-451 was calculated and the results are shown in FIG. 4. As shown, the isomiR's 1 and 3-7 showed little variation from the level of the miR-451 standard when the invention method was used. However, using either the Qiagen or TaqMan® approach, disparate results were obtained, in particular for isomiR 1 (sequence is shorter compared to miR-451) and 7 (sequence is shorter than miR-451).

TABLE 1

| microRNA Species IsomiR Sequence | SEQ ID NO: |
|---|---|
| miR-451 isomiR 1 AAACCGTTACCATTACTGA | 1 |
| miR-451 isomiR 7 AAACCGTTACCATTACTGAG | 2 |
| miR-451 isomiR 6 AAACCGTTACCATTACTGAGT | 3 |
| miR-451 miRBase AAACCGTTACCATTACTGAGTT sequence | 4 |
| miR-451 isomiR 5 AAACCGTTACCATTACTGAGTTT | 5 |
| miR-451 isomiR 4 AAACCGTTACCATTACTGAGTTTA | 6 |
| miR-451 isomiR 3 AAACCGTTACCATTACTGAGTTTAG | 7 |

EXAMPLE 2

Figure 5:
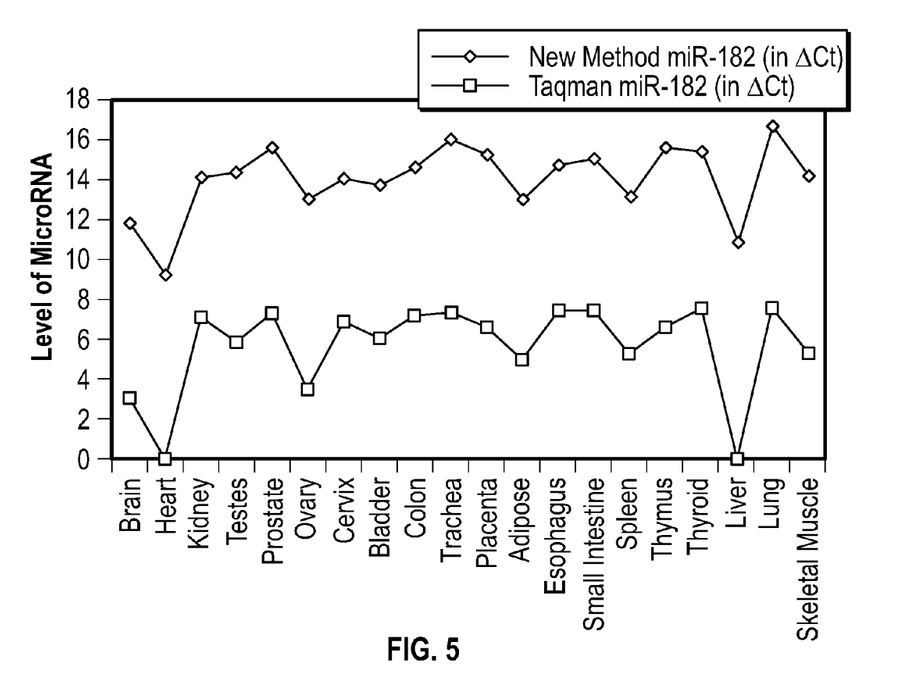
FIG. 5 shows results of comparison of the invention method with prior art QPCR in tissue samples.

Comparison of Different qPCR miRNA Detection Protocols with Tissue RNA Samples The TaqMan® qPCR and the invention method were also compared in measuring miR-182 levels in 20 different tissues. FIG. 5 shows the results where all tissues used in the example are listed on the X-axis while the miRNA levels are expressed on Y-axis (in log 2 value). As shown in FIG. 5, the results between TaqMan® method and the invention method gave very similar miR-182 profile across the 20 tissues; however TaqMan® method failed to detect miR-182 in either heart or liver, the method of the invention demonstrates that these miRNAs are in fact present. This probably caused by the existence of high concentration of miR-182 isomiR sequences in heart and liver and it has been demonstrated that the TaqMan® method is inefficient in detecting isomiR sequences as illustrated in Example 1. The method of the invention further showed higher miRNA levels in general.

The invention claimed is:

1. A method to determine the quantity of a target RNA in a sample, which method comprises:

providing extended molecules of said target RNA in said sample, wherein said molecules have been extended at the 5' terminus by a 5' adaptor nucleotide sequence and extended at the 3' terminus by poly A;

converting said extended target RNA into cDNA by reverse transcription using as primer an oligomer with the sequence: 3'-two-base-anchor-polyT-tag-5' to obtain an RNA:cDNA duplex;

directly annealing said RNA:cDNA duplex with a first primer consisting of 3'-sequence complementary to sequence at the 3' end of the target RNA, deoxynucleotide sequence complementary to polyA at the 3' terminus of the extended target RNA and optionally sequence of said tag and with a second primer that consists of 5' deoxynucleotide sequence identical to the sequence of the 5' adaptor and 3'-deoxynucleotide sequence corresponding to sequence from the 5' end of said target RNA; and quantitatively determining said target RNA by performing polymerase chain reaction (PCR) on said RNA:cDNA duplex using said first and second primers.

2. The method of claim 1 wherein the 5' adaptor or the tag contains deoxynucleotide "barcode" sequence to track sample identity.

3. The method of claim 2 wherein the deoxynucleotide "barcode" sequence is between 2 to 15 nucleotides in length.

4. The method of claim 1 wherein the quantitative determination of RNA is based on a next generation sequencing platform.

5. The method of claim 1 wherein the target RNA is microRNA.

* * * * *